United States Patent
Themis

(10) Patent No.: US 11,834,722 B2
(45) Date of Patent: Dec. 5, 2023

(54) METHOD OF TESTING A GENE THERAPY VECTOR

(71) Applicant: BRUNEL UNIVERSITY LONDON, Middlesex (GB)

(72) Inventor: Michael Themis, Middlesex (GB)

(73) Assignee: BRUNEL UNIVERSITY LONDON, Middlesex (GB)

( * ) Notice: Subject to any disclaimer, the term of this patent is extended or adjusted under 35 U.S.C. 154(b) by 433 days.

(21) Appl. No.: 16/629,521

(22) PCT Filed: Jul. 9, 2018

(86) PCT No.: PCT/GB2018/051937
§ 371 (c)(1),
(2) Date: Jan. 8, 2020

(87) PCT Pub. No.: WO2019/012259
PCT Pub. Date: Jan. 17, 2019

(65) Prior Publication Data
US 2021/0130915 A1     May 6, 2021

(30) Foreign Application Priority Data
Jul. 10, 2017   (GB) ..................... 1711065

(51) Int. Cl.
C12Q 1/70     (2006.01)
C12N 15/86    (2006.01)
C12N 5/071    (2010.01)

(52) U.S. Cl.
CPC .............. *C12Q 1/70* (2013.01); *C12N 5/067* (2013.01); *C12N 15/86* (2013.01); *C12N 2506/45* (2013.01); *C12N 2510/00* (2013.01); *C12N 2533/52* (2013.01); *C12N 2740/15043* (2013.01); *C12N 2750/14143* (2013.01)

(58) Field of Classification Search
None
See application file for complete search history.

(56) References Cited

U.S. PATENT DOCUMENTS

2016/0312304 A1   10/2016   Sorrentino et al.

FOREIGN PATENT DOCUMENTS

| WO | 2009140655 | 11/2009 |
|---|---|---|
| WO | 2010030461 | 3/2010 |
| WO | 2016120493 | 8/2016 |
| WO | 2013082509 | 6/2019 |

OTHER PUBLICATIONS

Papapetrou et al., Nat Biotechnol., Jan. 2011, 29(1):73-78. (Year: 2011).*
Nowrouzi et al., The American Society of Gene & Cell Therapy, Nov. 2012, 21(2):324-337. (Year: 2012).*
Themis (Charles Coutelle and Simon N. Waddington (eds.), Prenatal Gene Therapy: Concepts, Methods, and Protocols, Methods in Molecular Biology, vol. 891, 2012). (Year: 2012).*
Hong et al. (The American Society of Gene & Cell Therapy, Feb. 2013, 21(2):272-281) (Year: 2013).*
Ackermann et al., "Ex vivo generation of genetically modified macrophages from human induced pluripotent stem cells", Transfusion Medicine and Hemotherapy, 2017, 44:135-142.
Arens et al., "Bioinformatic Clonality Analysis of Next-Generation Sequencing-Derived Viral Vector Integration Sites", Human Gene Therapy Methods, 2012, 23:111-118.
Bokhoven et al., "Insertional Gene Activation by Lentiviral and Gammaretroviral Vectors", Journal of Virology, 2009, 83(1): 283-294.
Chandler et al., "Genotoxicity in Mice Following AAV Gene Delivery: A Safety Concern for Human Gene Therapy?", Molecular Therapy, 2016, 24(2):198-201.
Chen et al., "Transcriptome Comparison of Human Neurons Generated Using Induced Pluripotent Stem Cells Derived from Dental Pulp and Skin Fibroblasts", PLoS One, 2013, 8(10):e75682.
Godoy et al., "Corrigendum to 'Gene networks and transcription factor motifs defining the differentiation of human stem cells into hepatocyte like cells'", Journal of Hepatology, 2016, 64:525-526.
Hoffman et al., "Detailed comparison of retroviral vectors and promoter configurations for stable and high transgene expression in human induced pluripotent stem cells", Gene Therapy, 2017, 24:298-307.
Honda et al., "Generation of Induced Pluripotent Stem Cells in Rabbits", Journal of Biological Chemistry, 2010, 285 (41):31362-31369.
Kane et al., "Lentivirus-mediated Reprogramming of Somatic Cells in the Absence of Transgenic Transcription Factors", Molecular Therapy, 2010, 18(12):2139-2145.
Kim et al., "Differences between Cellular and Molecular Profiles of Induced Pluripotent Stem Cells Generated from Mouse Embryonic Fibroblasts", Cellular Reprogramming, 2010, 12(6):627-639.
Kustikova et al., "Cell-intrinsic and Vector-related Properties Cooperated to Determine the Incidence and Consequences of Insertional Mutagenesis", Molecular Therapy, 2009, 17(9):1537-1547.
Liu et al., "Enhanced tumor growth inhibition by mesenchymal stem cells derived from iPSCs with targeted integration of interleukin24 into rDNA loci", Oncotarget, 2017, 8(25):40791-40803.

(Continued)

*Primary Examiner* — Nicole Kinsey White
(74) *Attorney, Agent, or Firm* — James S. Keddie; Bozicevic, Field & Francis LLP

(57) ABSTRACT

A method of determining the safety and/or efficacy of a gene therapy vector prior to carrying out gene therapy on an individual includes infecting a culture of induced pluripotent stem cells obtained from the individual with a gene therapy vector. Ideally the cells are allowed to differentiate, and the infection is carried out at the start of culture and at least once during differentiation and/or after differentiation. Nucleic acids are extracted from the infected cells, and then analysed to measure and/or determine adverse effects of integration of nucleic acid from the vector and/or efficiency of expression of nucleic acid from the vector.

19 Claims, 6 Drawing Sheets

(56) References Cited

OTHER PUBLICATIONS

Montini et al., "Hematopoietic stem cell gene transfer in a tumor-prone mouse model uncovers low genotoxicity of lentiviral vector integration", Nature Biotechnology, 2006, 24(6):687-696.

Nowrouzi et al., "The Fetal Mouse Is a Sensitive Genotoxicity Model That Exposes Lentiviral-associated Mutagenesis Resulting in Liver Oncogenesis", Molecular Therapy, 2013, 21(2):324-337.

Paruzynski et al., "Genome-wide high-throughput integrome analyses by nrLAM-PCP and next-generation sequencing", Nature Protocols, 2010, 5(8):1379-1395.

Schmidt et al., "Polyclonal long-term repopulating stem cell clones in a primate model", Blood, 2002, 100 (8):2737-2743.

Schmidt et al., "Clonality analysis after retroviral-mediated gene transfer to CD34 cells from the cord blood of ADA-deficient SCID neonates", Nature Medicine, 2003, 9(4):463-468.

Schmidt et al., "High-resolution insertion-site analysis by linear amplification-mediated PCR (LAM-PCR)", Nature Methods, 2007, 4(12):1051-1057.

Scholz et al., "Lentiviral Vector Promoter is Decisive for Aberrant Transcript Formation", Human Gene Therapy, 2017, 28(10):1-11.

Themis et al., "Oncogenesis Following Delivery of a Nonprimate Lentiviral Gene Therapy Vector to Fetal and Neonatal Mice", Molecular Therapy, 2005, 12(4):763-771.

Wu et al., "Transcription start regions in the human genome are favored targets for MLV integration", Science, 2003, 300: 1749-1751.

Sugawara et al., "Investigating cellular identity and manipulating cell fate using induced pluripotent stem cells", 2012, Stem Cell Research & Therapy, 3:8, 1-10.

Doi et al., "Gene therapy using retrovirus vectors: vector development and biosafety at clinical trials", Uirusu, 2015, 65, 27-36.

Hanawa et al., "Gene therapy using retroviral vectors", 2003, Uirusu, 53, 177-183. This publication summarizes the state of the art of gene therapy using retroviral vectors in 2003.

* cited by examiner

METHOD OF TESTING A GENE THERAPY VECTOR

CROSS-REFERENCE TO RELATED APPLICATIONS

This application is a § 371 national phase of International Application No. PCT/GB2018/051937, filed on Jul. 9, 2018, which claims the benefit of United Kingdom Application No. 1711065.1, filed on Jul. 10, 2017, which applications are incorporated by reference herein.

This invention relates to a method of determining the safety and/or efficacy of a gene therapy vector. In particular, it relates to specifically determining the safety of gene therapy, its side effects and long term successful gene expression.

Gene therapy is a promising approach to deliver therapeutic genes by integration of the vector material carrying the gene permanently into the host genome of cells that require corrective gene augmentation. In this process fully functional genes can be used to treat or correct a genetic disorder where the existing gene in the diseased host is mutated and therefore not generating a functional protein. Gene therapy can deliver genes that provide proteins for normal cell function, for vaccination or to treat cancer by causing death of the target tumour cell(s). Gene therapy vectors that integrate nucleic acid into the target host genome include viruses such as adeno-associated (AAV), retrovirus (RV) and their subgroups. These prefer to insert themselves into open chromatin. Open chromatin is where genes are in an open or unwound configuration required for transcription. This configuration, which is representative of genes that are being expressed allows gene therapy vector entry for insertion. It has been shown that highly expressed genes are preferred targets for vector insertion (Kustikova et al. (2009), Wu et al. (2003), Nowrouzi et al. (2013)). The process of integration requires the host DNA to be cut so that nucleic acid carried by the virus vector can be inserted, then the repair of this process after linkage of the virus nucleic acid to the host is carried out by host DNA repair genes.

Previously, gene therapy suffered a set-back in which children that were treated for severe combined immune deficiency developed leukaemia. This was found to be associated with the therapeutic gene being carried by a retrovirus being inserted into a cancer gene, causing a change in its expression and leading to clonal outgrowth of cancerous cells carrying the integrated gene. Following this, several in vitro and in vivo models were designed to identify the contributory factors associated with the vector and its interaction with the host that led to clonal outgrowth of cells and oncogenesis. These known contributory factors include vector promoter or enhancer mediated activation of local genes of the host (believed to be limited to ~100 kb from the insertion site), splicing between the vector and host genes thereby generating truncated genes that may be uncontrolled in their expression, vector read-through where the promoter within a vector continues to drive the expression of a gene of the host near to vector insertion, and methylation of vector and of host genes by the host innate immune system. By methylating DNA, the host innate immune response aims to control the expression of the incoming foreign vector after infection to silence it, but this also results in methylation of its own genes thereby causing altered gene expression in the host of many important genes that control cellular homeostasis.

The applicant has previously developed an in vivo model in which foetal mice were treated with a retrovirus subgroup, lentiviruses (LV), that inserted into expressed host genes. These animals were allowed to come to birth, thereby exposing genes that were expressed during development to gene therapy vector integration. It was found that highly expressed genes were often chosen for integration and these mice went on to develop liver tumours. The applicant also found that this LV insertion occurred over a period of time during development, even after birth (measured up to 5 days post infection) (Nowrouzi et al. (2013)). In the foetal mouse, developmental genes include those involved in proliferation, growth and differentiation, and these are highly expressed. These types of genes are also known to be cancer genes or proto-oncogenes and are switched off usually after birth. Hence, integration of virus genetic material into and mutagenesis of these genes are suspected to have been the cause of cancer development in these animals.

The present invention seeks to provide an improved method of determining the safety and/or efficacy of a gene therapy vector.

According to an aspect of the present invention, there is provided a method of determining the safety and/or efficacy of a gene therapy vector including: infecting a culture of induced pluripotent stem cells with a gene therapy vector; extracting nucleic acids from the infected induced pluripotent stem cells; and analysing the nucleic acids to measure and/or determine adverse effects of vector integration and/or efficiency of gene expression by the vector.

This model mimics the situation during the developmental process, in which the genes expressed are involved in proliferation, development and differentiation. This method therefore allows testing of the vector with respect to cancer controlling genes. The method is carried out in vitro and provides an alternative to using animals in a method of testing a gene therapy vector.

The induced pluripotent stem cells are preferably derived from cells of an individual in need of gene therapy (Kane et al. (2010)). In an embodiment the cells may be provided from another individual to test vector side effects. The vector preferably carries the corrected gene that may or may not be required by the individual, along with any nucleic acid elements needed for its expression. In some embodiments, the vector carries a reporter gene (along with any nucleic acid elements needed for its expression.

In preferred embodiments, the induced pluripotent stem cells are allowed to differentiate, and the cells are infected with gene therapy vector at the start of culture, and at least once during and/or after differentiation.

This allows testing of the vector without being limited to genes expressed only at a single stage of development or differentiation by reaching many expressed genes over the developmental period and especially those associated with cancer that are important to the safety of gene therapy.

Preferably the culture is infected by the gene therapy vector at several different time points during differentiation.

The culture may be infected by the gene therapy vector at several different time points at the start and during differentiation to terminally differentiated cells to provide a wide range of gene targets to test vector safety and/or efficacy. This enables the safety of the vector to be tested on many genes. Infection at only a single time point would result in testing on only the few genes being expressed at that time.

In some embodiments, different amounts of vector are used in each infection.

The infecting step may include exposing the cells to vector for at least 30 minutes. For example, the infecting step may include exposing the cells to vector for at least 30 minutes (for example, for 30 minutes to 1 hour), for at least 3 hours (for example, for 3 to 6 hours), or overnight.

In embodiments, the infecting steps each include exposing the cells to vector at discrete time points during differentiation so that samples can be analysed for safety at each time point. The infecting step may enable the infection to be repeated on the same infected cells on several later occasions during the differentiation process.

The step of analysing the nucleic acids may include determining factors carried on the vector or resulting from its integration that potentially contribute to gene therapy side effects.

The determining may include analysis of the determining of vector insertion sites in the host genome, determining changes in gene expression of the gene with the nucleic acid from the vector inserted, determining new RNA transcripts or truncated RNA transcripts representative of vector/host gene splicing or vector promoter read-through, methylation changes to genes either with or near to the integration site of the nucleic acid from the vector, or not near to the integration site resulting in a change in expression, and/or determining inactivation of genes.

The vector may be a virus or plasmid. For example, the vector may be a retrovirus, a lentivirus, an adeno-associated virus and/or any integrating virus. The vector may be non-viral.

In embodiments, the induced pluripotent stem cells may be derived from a human.

The induced pluripotent stem cells may be derived from cells of an individual in need of gene therapy.

The vector may carry a corrected gene required by an individual, optionally with nucleic acid elements needed for expression of the corrected gene.

Preferred embodiments of the method involve exposing target cells to gene therapy vectors during the developmental period when stem cell differentiation to terminally differentiated cells occurs, during which time developmentally expressed genes are available for vector integration and mutagenesis.

Preferred embodiments of the present invention are described below with reference to, and as illustrated in, the accompanying drawings, in which.

Figure 1:
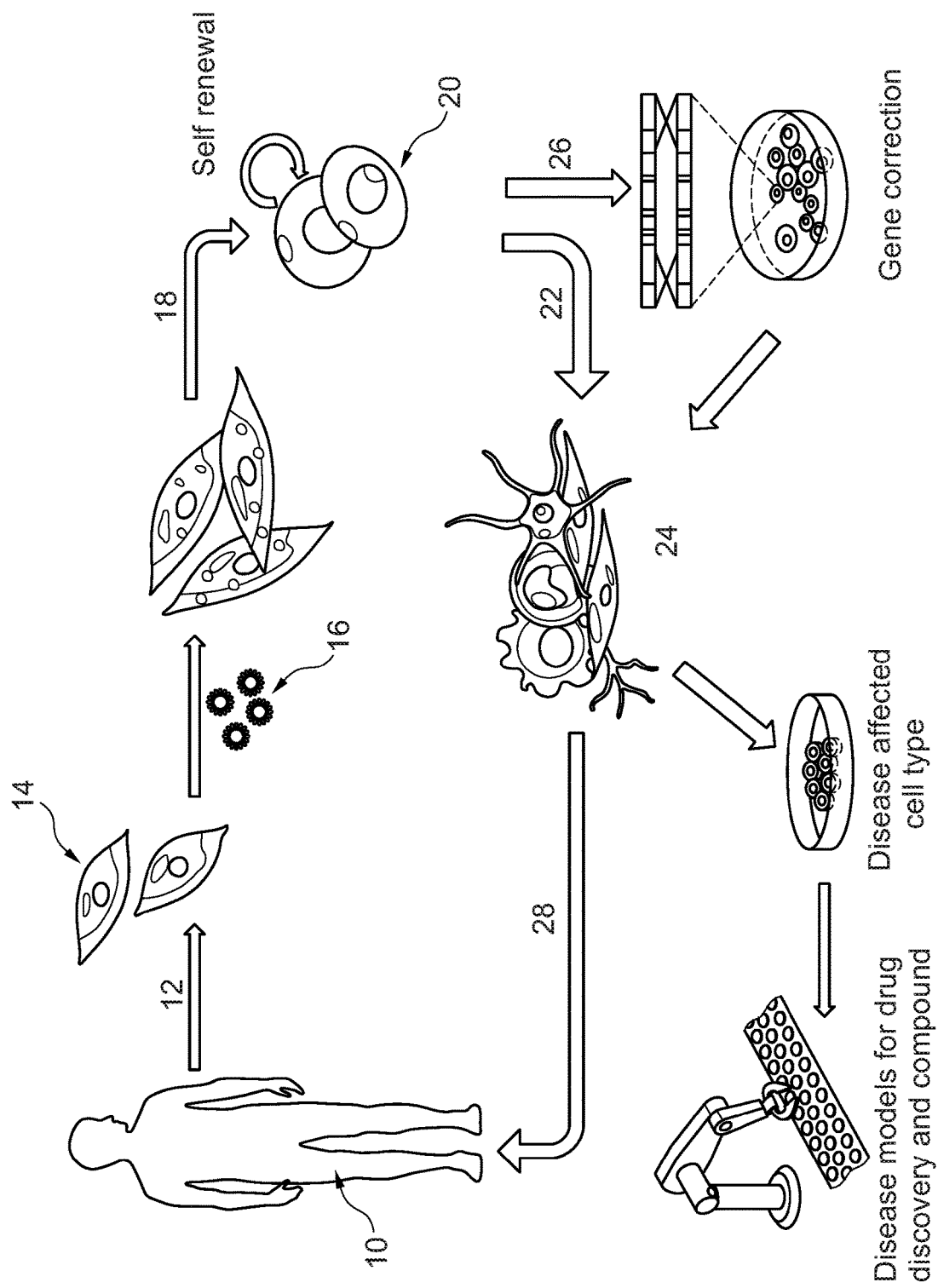
FIG. 1 illustrates generally the reprogramming of adult cells to iPSc and then to terminally differentiated cells.

The present applicant has developed an in vitro method that uses iPSc to mimic its prior in vivo model. The method uses stem cells, cells that are in the process of differentiation, and cells in their terminally differentiated forms for infection. At these stages genes that are active during this period to be available for integration by gene therapy vectors are provided. Using human cells, this method enables the side effects of gene therapy vectors to be measured in many genes in different configurations and also in genes that are considered cancer predisposing genes in humans. Preferred embodiments of the method use a range of molecular assays that expose changes in gene expression associated with integration. It may be considered as highly sensitive to genotoxicity and valuable to test the safety of these vectors before clinical consideration along with the efficacy of the gene therapy vector with respect to the expression of the gene carried by the vector over the differentiation period.

The method offers a safety test mimicking gene therapy in humans, but in a laboratory ie. the test is not invasive to the individual. The method allows developmentally expressed genes to be available to vector insertion in order to identify adverse side effects of gene transfer by integrating vectors.

The method also offers a personalised approach to determine adverse effects in the host from where the cells were originally obtained. In this process, normal cells such as fibroblasts from the host are converted to iPSc and then differentiated to terminally differentiated cells. Testing the vector for safety during this process by the method described here aligns the test of the vector configuration with the host's genetic background to test for mutagenesis and possibly oncogenesis specifically to the host as a personalised test. In an embodiment, the method can be carried out on iPSc and their differentiated counterparts obtained from cells derived from an individual other than the individual intended for gene therapy to test for vector safety.

This method allows vectors to be examined as safe before entering the clinic to treat patients with genetic disorders. It may also be used to find genes that cause cellular proliferation and cancer.

The method described here uses the fact that highly expressed genes are targeted for insertion by gene therapy vectors. The method uses an in vitro approach where iPSc are differentiated into several cell types such as of the liver, heart, nervous system and blood. During this time and depending on the differentiation route chosen, genes that are important to development into the cell types, which may be cancer genes (if made to be uncontrolled in their expression by the insertion of the nucleic acid carried by the vector), are expressed highly and open to integration by gene therapy vectors. This mimics gene therapy either ex vivo or in vivo because cell populations will be present that are at every stage of the developmental process and hence this in vitro method is representative for cells that are at each developmental stage, either at their early stage of development, on the way to terminal differentiation or terminally differentiated expressing genes that are vulnerable to integration by gene therapy vectors.

This method allows vector performance to be examined where the site of insertion into the host genome may be different each time and have an influence on successful gene expression of the genes carried on the vector.

The method described here uses iPSc and the steps to their differentiation to terminally differentiated cells and these cells grown after terminal differentiation to be infected at several stages during this process. Typically, different amounts of vector may be used during each infection. Nucleic acid carried by the vector will integrate into genes or regions of genomic DNA that are either being expressed or not expressed. Vectors target more genes or regions of genome DNA if it is highly expressed when the DNA is in open chromatin conformation as is usually the case when genes or regions of genome DNA are being transcribed. The infection procedure may or may not use agents to increase or improve the efficiency of infection to provide more infected cells or cells with higher numbers of vector integrants. Infection may involve exposure to vectors for a short period, typically 30 minutes to 1 hour or to longer periods of 1 or more days. After the chosen exposure period, the vector is washed off and the cells provided with medium to grow, or be harvested to isolate their DNA or RNA using standard protocols or commercially available kits.

The present method uses iPSc and their derivatives on their way to terminally differentiated cells (here to liver cells is used as an example) for infection at all stages for vector insertion. This provides the unique advantage of all genes being exposed to the vector so that samples of these cells can be used to measure changes in gene expression of genes influenced by the vector and therefore changes caused by the vector that are potentially contributory to gene therapy side effects. Assays for these factors are readily available such as one or more of:

(I) integration site analysis via ligation adaptor mediated PCR, target enrichment sequencing and inverse PCR on pools of infected cells or cloned infected cells.

(II) RNASeq on pools of infected cells or cloned infected cells that measures the levels of RNA transcripts in infected versus uninfected cells and hence gene expression changes that occurred after infection to show the influence of vector promoter or enhancer activity on genes. RNASeq also provides information on the presence of novel RNA spliced transcripts between the vector and host genes and transcripts arising from read-through from the vector promoter within the vector outward to host genes.

(III) q-RTPCR with primers designed for the gene where the vector integration site is known to measure specifically changes in expression of that gene, which requires a clonal cell population of this cell/IS to be isolated.

(IV) DNA methylation by ELISA or other means to measure CpG methylation of vector and host DNA that, based on previously published work, provides evidence that genes that are methylated may be altered in expression.

For these routine assays sample cell populations can be harvested at any time after infection for example between the start and the end of differentiation process for assay.

This differentiation model closely matches the developmental process in humans and offers genes controlling this process or other genes to be readily available for integration. This method provides a platform that tests the safety of the integrating vector by allowing for the vectors to be examined for either no effect or adverse effects on the host and useful before considering the use of the vector in the clinic for the treatment of disease. The system can be tested in several cell routes to differentiation and offers a systems approach using bioinformatics across these cell types that characterises vectors as able or not able to cause adverse side effects.

FIG. 1 illustrates generally the reprogramming of adult cells to iPSc and then to terminally differentiated cells. Adult cells such as fibroblasts 14 can be obtained from an individual donor/patient 10 by biopsy 12 and converted to iPSc using transcription factor programming genes 16 such as Oct4, Sox2, c-Myc, and Klf4, and induction of pluripotency 18. The resulting iPSc 20, which resemble embryonic stem cells, can then be differentiated 22 to terminally differentiated cells 24 such as hepatocytes. During this process, the cells may be infected 26 with a gene therapy vector. Because, in these cells, several genes controlling this process are actively being transcribed and in open chromatin conformation, these genes are highly preferred for virus entry for integration. This enables multiple genes to be accessible and available for mutagenesis, by the vector. Because many gene targets are available, this provides a sensitive model for testing the effects of gene therapy vector configurations and hence the safety of the vector using, for example, one or more of the above-mentioned molecular methods that identify vector insertion sites, and altered expression of the genes with or without these insertion sites. This also tests the efficacy of gene transfer and longevity of gene expression by the vector throughout the differentiation process.

In a method of gene therapy, corrected cells are then transplanted 28 back into the individual 10.

In preferred embodiments of the present invention, instead of being transplanted back into the individual, the corrected cells are analysed in order to profile vector safety. Specifically, nucleic acids from the cells are analysed to measure and/or determine adverse effects of integration of nucleic acid from the vector and/or efficiency of expression of nucleic acid from the vector.

Figure 2:
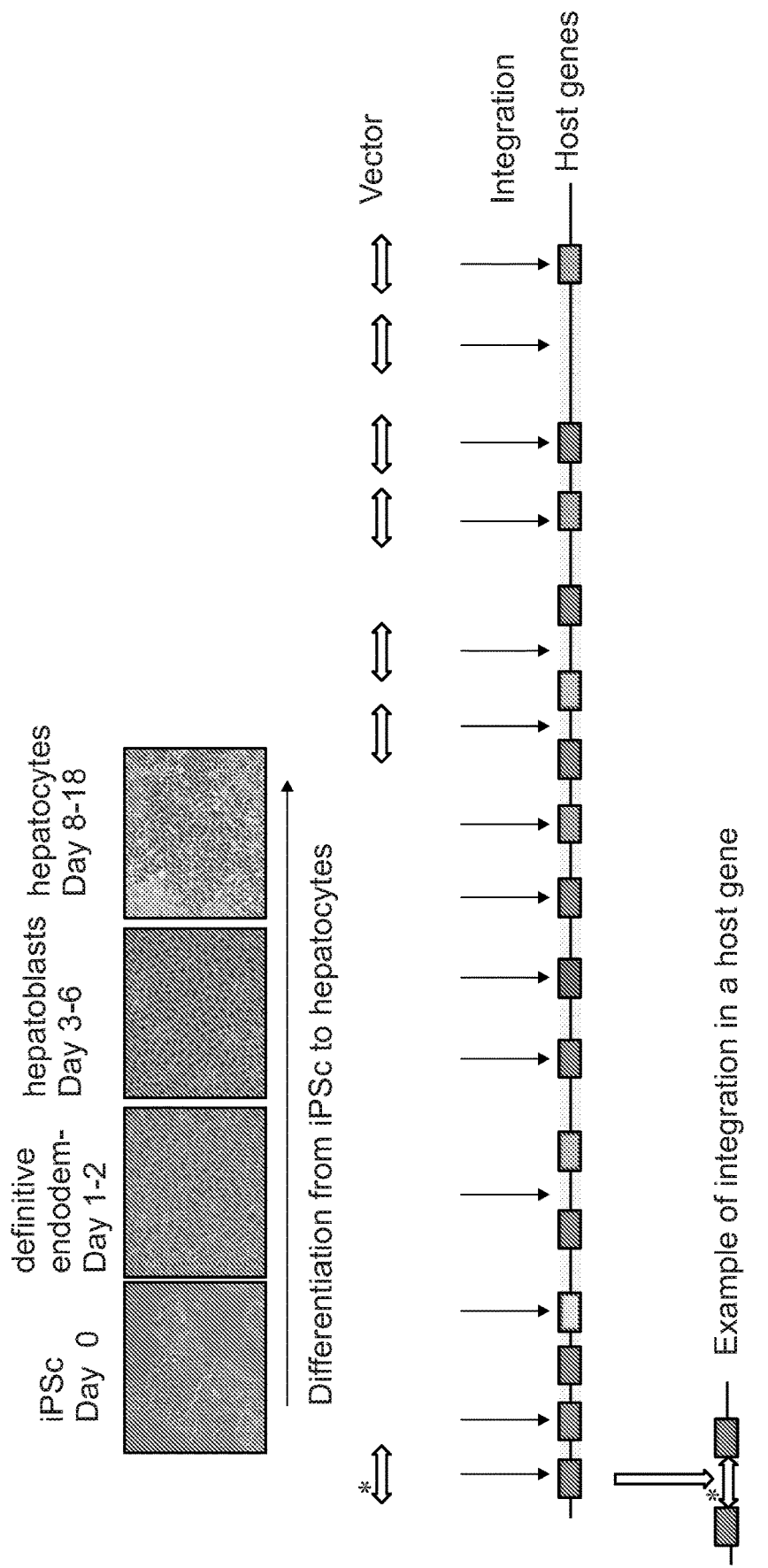
FIG. 2 is a schematic diagram of multiple gene expression during iPSc to liver differentiation, vector integration and mutagenesis.

FIG. 2 is a schematic diagram of multiple gene expression during iPSc to liver differentiation, vector integration and mutagenesis. It shows cells can be differentiated from iPSc to hepatocytes. It shows vector integration during iPSc to hepatocyte differentiation in or near to host genes. During this time many genes are actively expressed and in this state are vulnerable to gene therapy vector integration. Genes associated with cancer are switched on and off during development and expressed at different levels. Highly expressed genes are more vulnerable to insertion by the vector. This can lead to mutagenesis. This scenario mimics in vivo gene therapy. During the development, this wide range of genes are known to be associated with cancer. Since they are highly expressed they are open to integration. This means after insertion of the vector these genes can be tested for vector effects on expression of the insertion site genes and therefore this method tests more thoroughly the safety of the vector in several different genes types in their unique configurations.

Previously no in vitro method existed where multiple genes, important to the control of cancer or normal cellular behaviour, are highly expressed at one time that would be vulnerable to mutagenesis if exposed to gene therapy vector (as had been demonstrated in the in vivo foetal mouse model). The in vitro model described here mimics gene delivery to humans in vivo where many cells are at several developmental stages which could be interrupted by integration following vector administration. By infecting stem cells whilst they are being converted to terminally differentiated cells, this offers all the genes being expressed during this time to be available for vector integration and therefore mutagenesis. Since many developmental genes are known to be cancer associated, which are usually switched off after birth, this makes the scenario of infection during differentiation representative of gene therapy in vivo where integration can occur into early and late developmental cell types.

In turn, as mentioned, this offers genes vulnerable to mutagenesis, and therefore tests whether the configuration of the gene therapy vector could cause the contributory effects known to be associated with vector adverse effects and oncogenesis.

EXAMPLES

Example 1—Infection of iPSc During Differentiation to Hepatocytes

Method

The Example below uses the protocol described by Szkolnicka et al. (2014) for pluripotent stem cell differentiation to hepatocytes. This method is used here for infection by gene therapy vectors during this differentiation.

Typically:
1. Cell culture plates are coated with 10 ml Matrigel BD (Matrigel (BD Bioscience, Matrigel, cat. no. 354230) made with knockout DMEM (KO-DMEM; Life Technologies, cat.no. 10829) in sterile 30-ml universal tubes. 1 ml matrigel in 18 ml KO-DMEM is used to obtain 1 ml mixture for each well of a 6 well plate.
2. The 6 well plate is coated with human recombinant vitronectin (cat. A14700; Life Technologies). A 60 ml aliquot of vitronectin is pipetted into a 15-ml conical tube containing 6 ml of sterile DPBS without calcium and magnesium (cat. 14190) at room temperature and 1 ml of the diluted vitronectin solution is added to each well and plates are room temperature for 1 hour before use.
3. The plates are then coated with lamins (refer to Bio-lamina website for coating instructions) using Laminins 521/111 mix (L111). Laminin 521 (100 ug/ml) and Laminin 111 (100 ug/ml) (Biolamina (Sweden). A concentration of 5 ug/cm$^2$ laminin 111 mix (a blend of 521 and 111, at a 1:2 or 1:3 ratio) is used. Laminins dilution uses PBS containing calcium and magnesium. Plates are incubated at 37° C. for 2 hours after plating.
4. iPSc can be maintained on vitronectin plates in Essential 8 medium (E8; Life Technologies) 2 ml per well. The medium must be aspirated each day and replaced with 2-3 ml of fresh medium per well. Cells passaging takes place every 3-4 days using EDTA (1:1000 dilution; Life Technologies) at 1:3 ratio.
5. Cell can be infected at various densities e.g. can be infected per well at an MOI of between 1-10,000 of gene therapy vector (concentrated so as not to alter the composition of the growth medium significantly) depending on the vector either with or without agents such as polybrene (usually 5 μg/ml vol) to enhance infection. Infection typically occurs for 3-6 hours after which time the vector is removed and replaced in fresh medium. After a 24 hours expression time, the cells can be removed from each well using Gentle Cell Dissociation Reagent (Stem Cell Technologies, cat. no. 07174) and a scraper and DNA and RNA purified from the cell using a commercially available kit. Ideally one well is used for DNA and another to isolate RNA. This material will be subject to molecular assays as described at the end of this method.
6. To differentiate the cells, the medium is aspirated from iPSCs once they have reached approximately 70% to 80% confluency. The cells are washed with PBS and treated with 1 ml Gentle Cell Dissociation reagent for approximately for 6 to 8 min at 37° C. until cells start to detach.
7. Cell suspension are transferred to a 15 ml sterile tube containing an equal volume (1 ml) of DMEM/F12, centrifuged for 5 min at 1000 rpm at room temperature and the supernatant is aspirated followed by resuspension of the cells in 1 ml of E8 containing ROCK inhibitor (Y-27632) to a final concentration of 10 μM.
8. Cells should be counted with a hemacytometer and diluted to a density in E8 of 10$^5$ viable cells per cm$^2$ for hepatocyte differentiation experiments. Cell suspensions are added to the E8-containing wells and incubated at 37° C. and ROCK inhibitor (Y-27632 (ROCK inhibitor; Stem Cell Technologies, cat. no. 07171) gently for ~30 sec to distribute the cells in the well. Cell should be maintained at 37° C. and 5% CO$_2$ for 24 hr to allow the cells to attach to the specific matrix of choice (matrigel/vitronectin/laminin mix).
9. Human pluripotent stem cell differentiation
    The protocol describes how to efficiently differentiate iPSc to hepatocytes with ~90% of cells expressing albumin and display cytochrome P450 activity. One well of a 6-well plate at 80% confluency usually contains ~3×10$^6$ viable cells.

Day 0, 1, and 2 of Differentiation-Definitive Endoderm
Dissociate cells into single-cell suspension (as described above). Count cells and seed at 10$^5$ viable cells per cm$^2$. Cells are differentiated usually 24 hrs after seeding and should be evenly distributed. Initial cellular differentiation should be at a cell density of 20% to 30% (determined by phase microscopy).
Prepare the required volume of RPMI/B27 supplement with (50 ng/ml) recombinant mouse wnt3a (R&D Systems, cat. no. 1324-WN-500/CF; see recipe) Use 2 ml/well and ensure the medium has reached room temperature before use. Aspirate the spent E8 medium from hiPSCs. On day 0, wash the cells gently with RPMI/B27 medium (without wnt3a and AA) before adding fresh RPMI/B27 medium supplemented with wnt3a and AA. Note: The cells may need to be washed with RPMI/B27 medium (without wnt3a and AA) on day 2 and day 3 due to the high cell death. Otherwise, the cells do not need to be washed before changing to fresh RPMI/B27 medium supplemented with wnt3a and AA. Remove spent medium and add appropriate volume of RPMI/B27/wnt3a/AA on days 0, 1, and 2. Gene therapy vector may be added as described above at this point and material harvested as described in Step 5 of this method.

Day 3, 4, and 6 of Differentiation-Hepatoblasts
Prepare 4 ml/well SR/DMSO medium (see reagents and solutions below).
Aspirate the RPMI/B27 medium from the cells and add SR/DMSO medium on day 3, 4, and 6. The cells may not need to be washed on day 4 and 6 before changing the medium unless there are noticeable dead cells which need to be removed, in which case cells should be gently washed with SR/DMSO. Gene therapy vector may be added on each day as described above at this point and material harvested as described in Step 5 of this method.

Day 8, 10, 12, 14, 16, and 18 of Differentiation-Hepatocyte Specification
Prepare 4 ml/well of HZM medium supplemented with 10 ng/ml HGF and 20 ng/ml OSM (see reagents and solutions below) and ensure the medium is at room temperature before use. Aspirate off the medium from the cells and on day 8, wash the cells with HZM without supplements. Add HZM medium supplemented with HGF and OSM every 48 hr until day 18. Cells can be examined for hepatic markers by routine assays or using kits. Gene therapy vector may be added on each day as described above at this point and material harvested as described in Step 5 of this method.

Materials
Human iPSc (hiPSc) in 6-well Matrigel-coated plates RPMI/B27 differentiation medium (see recipe; Reagents and Solutions section) SR/DMSO differentiation medium (see recipe; Reagents and Solutions section)
HepatoZYME (HZM) differentiation medium (see recipe; Reagents and Solutions section) Recombinant mouse wnt3a (R&D Systems, cat. no. 1324-WN-500/CF; see recipe)

Human Hepatocyte Growth Factor (HGF; Peprotech, cat. no. 100-39; see recipe Reagents and Solutions section)

Human Oncostatin M (OSM; Peprotech, cat. no. 300-10 (see reagents and solutions below)

Reagent and Solutions

SELECTED SUPPLIERS OF REAGENTS AND EQUIPMENT.

Maintenance medium for pluripotent stem cells

E8 and supplement (Life Technologies, cat. no. A1517001)

ROCK inhibitor Y-27632 (ROCK inhibitor; Stem Cell Technologies, cat. no. 07171), Y-27632 should be prepared at a 5 mM stock concentration in sterile water, aliquoted, and stored in the freezer until use.

RPMI 1640/627 differentiation medium, RPMI 1640 (Life Technologies, cat. no. 21875) 1°—final concentration of B27 supplement (from 50°—B27 supplement stock; Life Technologies, cat. no. 17504)

1%—penicillin/streptomycin (pen/strep; Life Technologies, cat. no. 15140; add from 100°—concentrated stock)

50 ng/ml final concentration of recombinant mouse wnt3a (R&D Systems, cat. no. 1324-WN-500/CF; from stock wnt3a prepared at 10 μg/ml in 0.2% BSA in PBS)

100 ng/ml final concentration of human activin A (AA; Peprotech, cat. no. 120-14E; from stock AA prepared at 100 μg/ml in 0.2% BSA in PBS). SR/DMSO differentiation medium Knockout DMEM (KO-DMEM; Life Technologies, cat. no. 10829)

Knockout Serum Replacement (KO-SR; Life Technologies, cat. no. 10828) Make sure that Knockout Serum Replacement is 20% of the whole medium (1:5 ratio KOSerum: KO-DMEM)

0.5%—GlutaMAX (Life Technologies, cat. no. 35050; add from 100°—concentrated stock), 1% non-essential amino acids (NEAA; Life Technologies, cat. no. 11140; from—concentrated stock)

0.1 mM final concentration of 2-mercaptoethanol (from 50 mM stock; Life Technologies, cat.no. 31350)

1% (v/v) DMSO (Sigma-Aldrich, cat. no. D5879)

1%—penicillin/streptomycin (pen/strep; Life Technologies, cat. no. 15140; add from 100°—concentrated stock)

HepatoZYME differentiation medium

HepatoZYME medium (HZM; Life Technologies, cat. no. 17705)

1%—GlutaMAX (Life Technologies, cat. no. 35050; add from 100%—concentrated stock)

10 μM final concentration of hydrocortisone 21-hemisuccinate sodium salt (HC; Sigma-Aldrich, cat. no. H4881; from stock HC prepared at 1 mM in PBS)

1%—penicillin/streptomycin (pen/strep; Life Technologies, cat. no. 15140; add from 100%—concentrated stock)

10 ng/ml final concentration of human Hepatocyte Growth Factor (HGF; Peprotech, cat. no. 100-39; from stock HGF prepared at 10 μg/ml in 0.2% BSA in PBS)

20 ng/ml final concentration of human Oncostatin M (OSM; Peprotech, cat. no. 300-10; from stock OSM prepared at 20 μg/ml in 0.2% BSA in PBS)

RPMI/B27, SR/DMSO media and stock factors must be filtered prior to use. HepatoZYME (HZM) does not require filtering. Concentrated stock solutions of growth factors were diluted to the final working concentrations in the appropriate cell culture medium Infected cells can then be subjected to one or more assays to determine vector toxicity. These assays might include determining the sites (genes or near to genes) at which the vector integrates, the effect of the vector of gene expression of the gene with the insertion, into or near to it, whether or not the vector splices with the host genomic nucleic acid generating novel genetic transcripts, whether the vector reads through to change the expression of a nearby gene, and/or whether the infection/integration causes DNA damage or epigenetic changes that result in altered gene expression of cellular homeostasis. Infected cells may be monitored for outgrowth of dominantly acting clones representative of mutagenised cells or cancerous or pre-cancerous cells.

Example 2—Identification of Vector Insertion Sites, Fusion Transcripts and Read-Through Example 2 shows how vector insertion sites may be identified. It describes how vector integration into or near to genes enables identification of the neighbouring nucleic acid near to the insertion sites and hence the genetic locus of the integrated nucleic acid from the vector. Briefly, the methods use PCR amplication and enrichment to amplify the DNA next to the insertion sites. This DNA is then isolated, cloned and sequenced. BLAST of this sequence against the human genome then allows the position of the vector to be identified. If this is an important gene associated with cancer, this provides some evidence that the gene may be available for mutagenesis by the vector such as by splicing, readthrough or gene inactivation of this gene. Hence, insertions in important genes involved in cancer is an indication of potential genotoxicity. The position of the vector is also influenced by its configuration and therefore different vectors have different potential to mutagenesis (Scholz et al. (2017)). Preferred embodiments of the present method expose numerous genes for this process to occur and is therefore more sensitive to test gene therapy vector adverse effects.

Methods

Amplification of Vector-Genomic DNA Junctions.

Genomic DNA was extracted from infected cells and LAM-PCR: linear amplification for the LV vectors was performed as previously described (Themis et al. (2005) and Schmidt et al. (2002)). LAM-PCR of genomic DNA adjacent to the vector was also performed using 100 ng of genomic DNA and 2.5 U Taq polymerase using the following two biotinylated primers of sequences found in the 5' LTR: to a 50 μl final volume. Cycle parameters of 95° C. for denaturing for 5 minutes (single cycle) followed by 95° C. for 60 seconds, 60° C. for annealing for 45 seconds and 72° C. extension for 90 seconds for 50 cycles, 72° C. for 10 minutes. 2.5 U additional Taq polymerase was added and the PCR run for another 50 cycles. PCR products were captured using the Dynabeads kilobase binder kit (Dynal, Oslo, Norway) and the second DNA strand was synthesised using Klenow (Invitrogen, Carlsbad, CA) with random hexanucleotides (Invitrogen, Paisley, UK) (20 μl reaction mixture) at 37° C. for 1 hour. The double stranded DNA was digested with a regularly cutting enzyme such as Tsp509I and a linker oligonucleotide added followed by ligation with Fast Link DNA Ligase kit (Epicentre Technologies, Madison, Wisconsin) for 15 minutes at room temperature. The DNA was denatured with 0.1 mol/l NaOH before two rounds of PCR using the same conditions as the linear amplification with primers. PCR products were separated on 3% agarose gels and DNA fragments were isolated using a Quiex II gel extraction kit (Qiagen, Crawley, UK) and cloned into a TOPO TA plasmid cloning kit (Invitrogen) as per the manufacturer's instructions3. Bacterial colonies containing DNA fragments corresponding to those seen in the second round PCR were sequenced using the LV-specific nested primer. EIAV and HIV-insertion sites cloned by LAM PCR and nonrestrictive PCR techniques obtained using 100-300 ng of sample genomic DNA were sequenced by deep parallel pyrosequencing (GS FLX/454: Roche, Mannheim, Germany) then subjected to Blas2Seq and the Smith-Waterman algorithm as previously described (Montini et al. (2006)). Sequences were aligned with the mouse genome using UCSC BLAT genome browser or BLAST.

The molecular function and role in biological processes of each integration near to or within a RefSeq gene (within a 100 kb window) was determined using the Gene Ontology database and identified with potential to be a candidate gene involved in tumorigenesis.

Randomised Data Set Generation

To assess whether insertion sites where assigned to chromosomes randomly, randomisation was carried out 100 times to yield 100 randomised counts of vector inserts per chromosomes. A t-test (95% confidence) was performed between the single observed count of sites per chromosome and the randomised population of 100 counts. Similarly, for CG content and gene density statistics, randomised data were generated across the genome. To determine the nature of vector insertion distances from transcription start site and regions within genes, t-tests were performed between observed data and those data generated from sites assigned to random locations, 100 times, within the gene.

Analysis of Biological Networks by Ingenuity Pathway Analysis (IPA)

Network analysis was performed on lists of genes generated from the earlier analyses described above as being differentially expressed. IPA (Ingenuity Systems, Redwood City, CA) that contains data of individually curated relationships between gene objects (e.g., genes, mRNAs, and proteins) was used for the identification of the biological processes that are significantly overrepresented to generate significant biological networks and pathways. Statistical significance of the biological overrepresentation was determined using Fisher's exact P value based on the relative overrepresentation of a minimum of three genes in the particular pathway as compared with a random sample of genes (P value cut-off of <0.05). Scores corresponding to P<10-20 or lower after Benjamini Hotchburg correction were used to select highly significant biological networks.

Gene Expression Analysis

Figure 3:
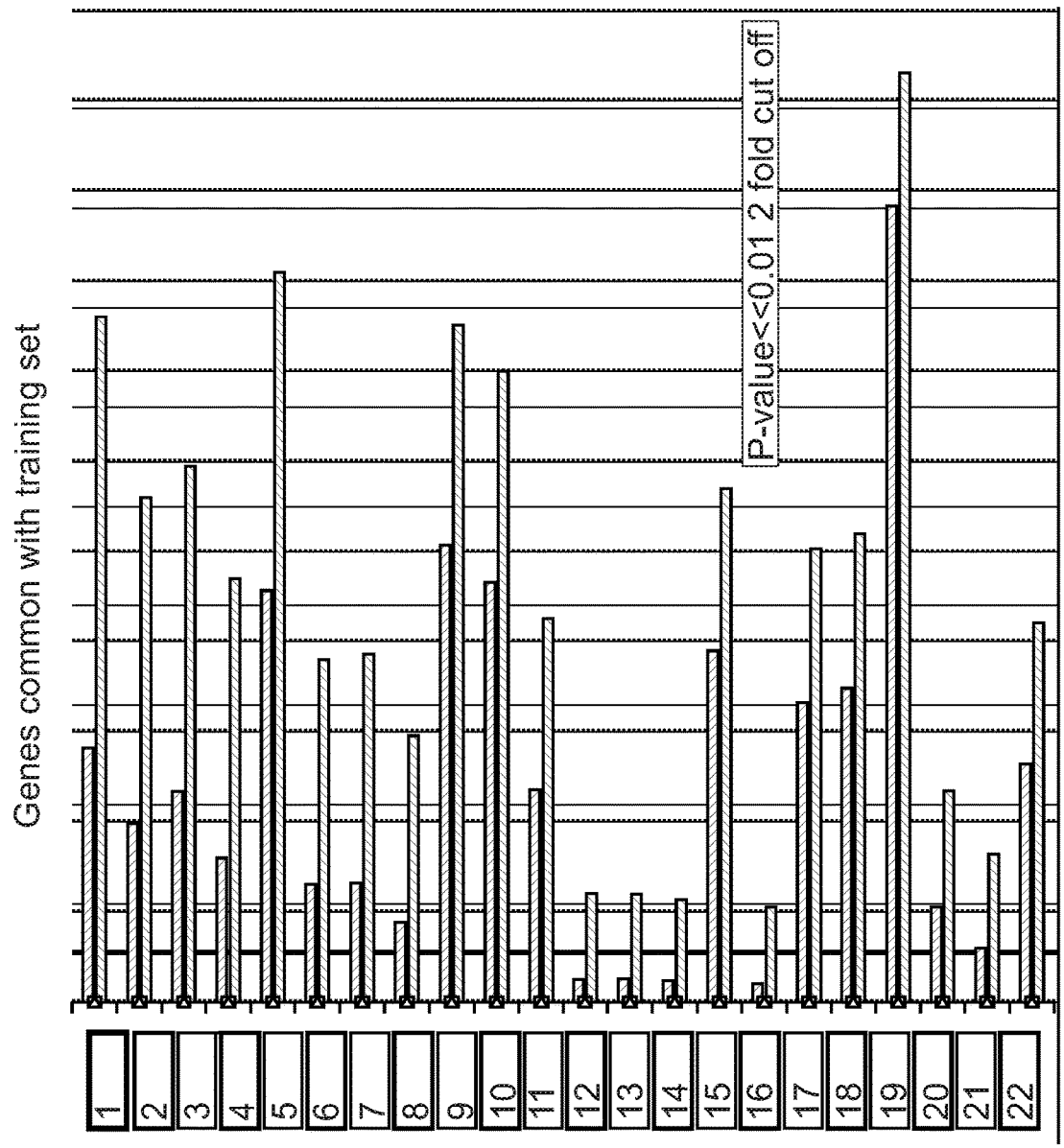
FIG. 3 shows genes involved in important pathways that are elevated in expressions between iPSc compared to hepatocytes.
Figure 4:
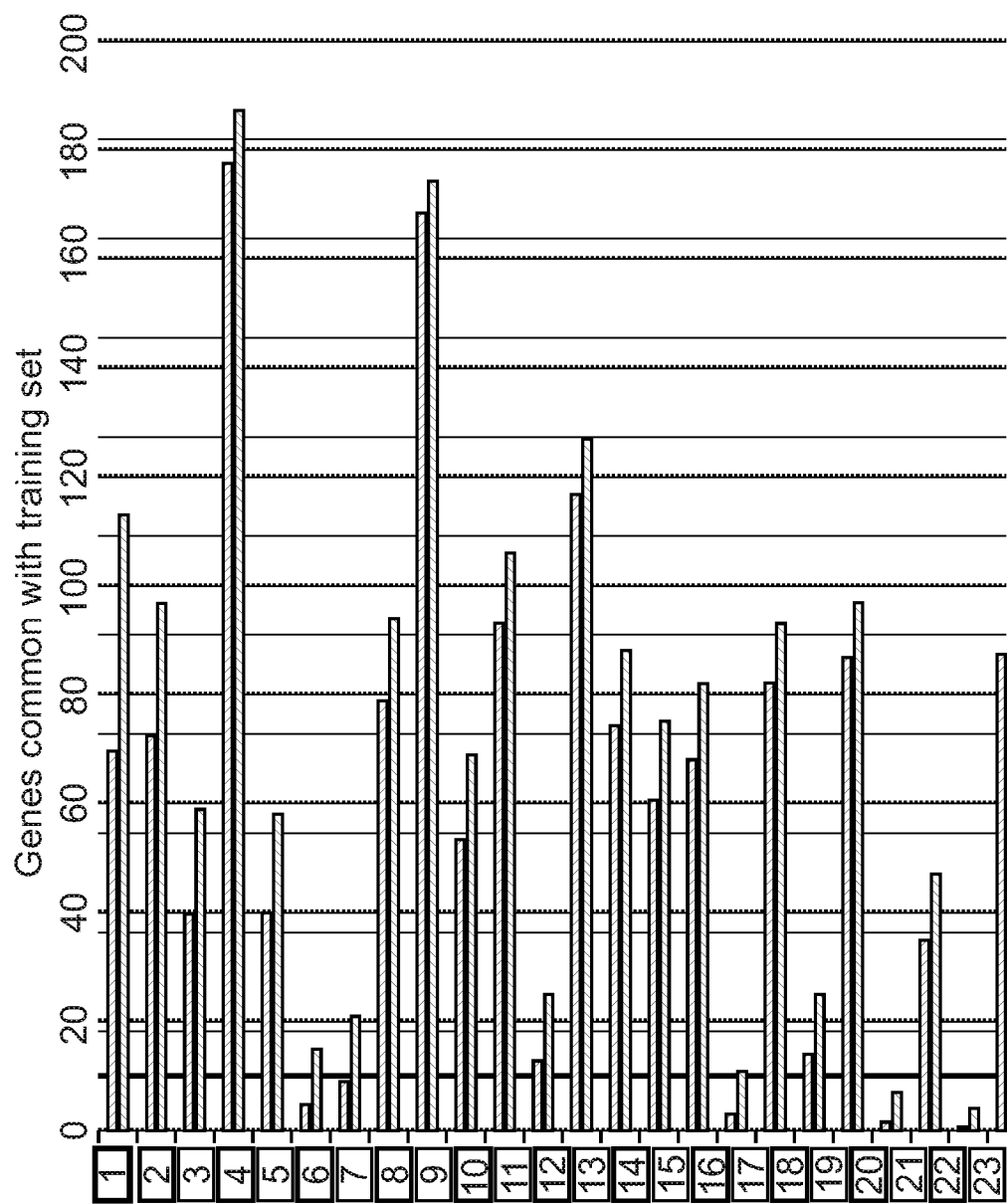
FIG. 4 shows gene ontologies of iPSc versus hepatocytes that are enriched in expression.

Gene expression analysis can be performed by several methods that are commercially available. By firstly isolating cellular RNA from cells under investigation, these RNAs can be converted to cDNA using reverse transcriptase and then subjected to microarray, using already prepared probes to cDNAs to measure the abundance of these cDNAs. RNASeq is a method that is also commercially available that directly sequences RNA transcripts and measures their relative abundance in cells under investigation. These methods are useful to determine changes in gene expression levels in cells that have been infected with gene therapy vectors compared with cells that have not. Shown in FIGS. 3 and 4 are the analyses of genes upregulated in iPSC cells compared to hepatocyte-like cells based on the difference in the gene expression of these genes between these developmental periods using a cut off of 2-fold upregulation between the two with a significant p-value.

The data for these analyses were obtained from microarray data that was obtained using Affymetrix GenChip Human Genome HG-U133 plus 2.0 chips and was obtained from Table 2 from Godoy et al. (2016), which provides information on gene sets that are differentially expressed. The data are shown in FIGS. 3 and 4.

Tables 1 and 2 below provide the key for the data shown in FIGS. 3 and 4.

TABLE 1

| Disease | |
| --- | --- |
| Metabolic process | 1 |
| NcRNA processing | 2 |
| Ribonucleoprotein biogenesis | 3 |
| Ribsome biogenesis | 4 |
| RNA process | 5 |
| rRNA processing | 6 |
| rRNA metabolism | 7 |
| tRNA processing | 8 |
| Mitotic cell cycle | 9 |
| Cell cycle processing | 10 |
| Regulation gene expression | 11 |
| Aminoacetylation | 12 |
| Amino Acid activation | 13 |
| tRNA Translation | 14 |
| Biosynthesis processing | 15 |
| rRNA maturation | 16 |
| Translation | 17 |
| Peptide processing | 18 |
| Cell cycle | 19 |
| RNA localisation | 20 |
| tRNA processing | 21 |
| Mitotic phase transition | 22 |

| Disease | |
| --- | --- |
| Liver cirrhosis | 1 |
| HIV infection | 2 |
| Neoplams of mouth | 3 |
| Mammary neoplasms | 4 |
| Oral carcinoma | 5 |
| Sensory impairment | 6 |
| Weight gain | 7 |
| Cervical cancer | 8 |
| Glioglastoma | 9 |
| Breast cancer | 10 |
| Cervix carcinoma | 11 |
| Mammary neoplasm | 12 |
| Malignancy | 13 |
| Cervix tumours | 14 |
| Adenocarcinoma | 15 |
| Nasopharyngeal carcinoma | 16 |
| Infection | 17 |
| Head and neck cancer | 18 |
| Mammary cancer | 19 |
| Lung adenocarcinoma | 20 |
| Eosophageal enosis | 21 |
| Invasive breast cancer | 22 |
| Dental colour abnormal | 23 |

FIGS. 3 and 4 shows that during iPSc to hepatocyte differentiation many genes are active (rather than at the hepatocyte stage only). They show differences in gene expression between iPSc and hepatocytes as useful targets for integration and hence available to test the effects of the vector.

These data show iPSc versus hepatocytes (Hhe) (2-fold upregulation with significant p-value). Several genes important to cellular pathway such as cellular proliferation, growth and cancer are enriched more so at the iPSc stage compared to the Hep stage. Infection at both stages should preferably be carried out to test for vector side effects.

FIG. 3 shows bioinformatics, using top gene, which enables enriched gene lists to be analysed to determine the involvement of the genes in important pathways. These genes are those that were found elevated in expression between iPSc versus Hepatocytes and considered targets for vector insertions after infection.

FIG. 4 shows gene ontologies of the genes shown in FIG. 3. Several genes important to cellular processes such as cellular proliferation, growth and cancer are highly expressed more so at the iPSc stage compared to the Hepatocyte stage. Infection at both stages should preferably be carried out to test for vector side effects.

Figure 5:
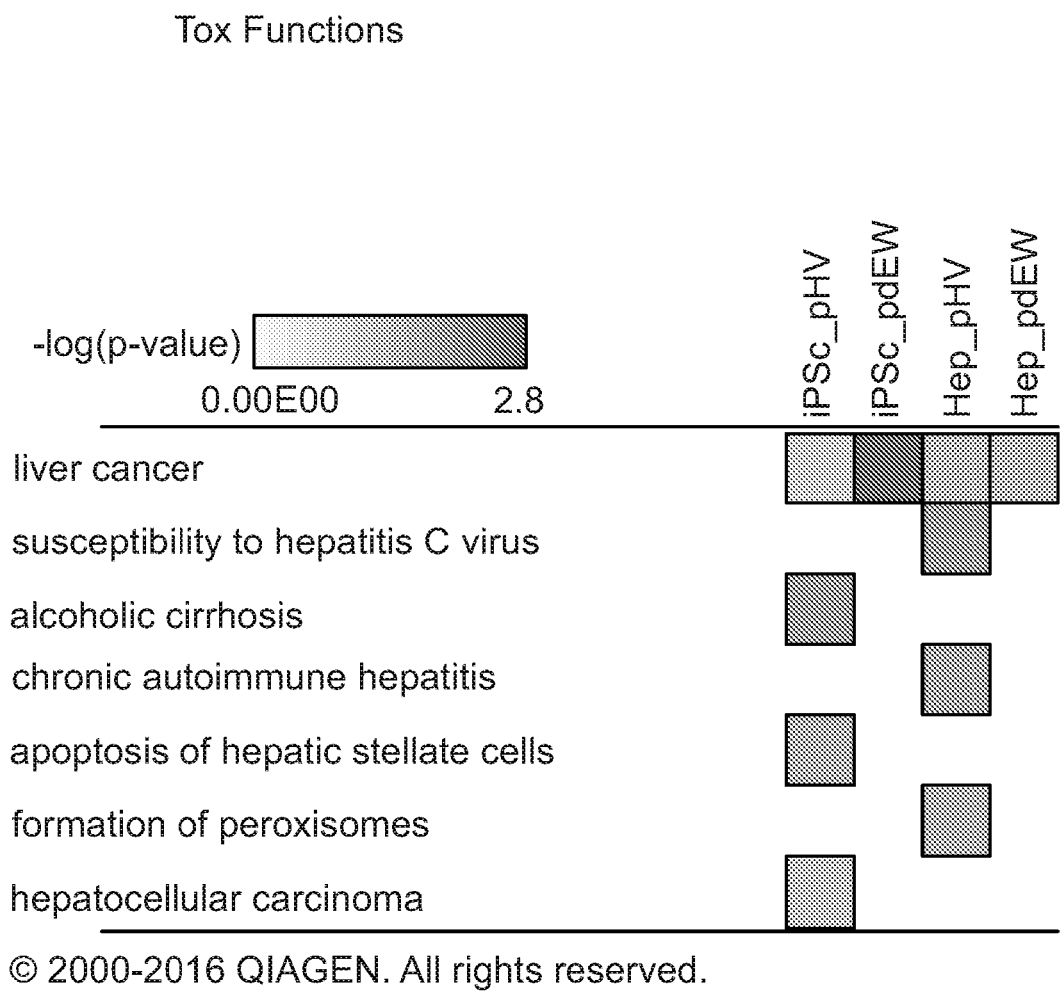
FIG. 5 is an Ingenuity Pathway Analysis (IPA) of inserted genes by LV vectors pHV and pdEW each carrying a green fluorescent protein (GFP) reporter gene.

Genes can be also analysed using Ingenuity Pathway Analysis (IPA) (www.ingenuity.com/products/ipa/toxicogenomics) to perform pathway analysis of genes, subpathways and networks, predict molecule interaction and to predict whether significant biological processes are increased or decreased based on gene expression data. FIG. 5 shows IPA of inserted genes by LV vectors pHV and pdEW each carrying a GFP reporter gene. Genes that are involved in several toxicological pathways and processes have insertions. The gene ontologies of these genes show that infection at both the iPSc and hepatocyte (Hep) stages are important for vector insertions into these genes and that genes with insertions after infection at the both stages (more so in iPSc) are important in the cancer process. FIG. 5 also shows that different vectors target different genes for integration. Although these results were obtained from iPSc and hepatocytes, the same methodology can be performed on any type of infected cell.

Further assays relating to splicing, readthrough, outgrowth and other methods are known to the skilled person and may alternatively/additionally be carried out. Such methods demonstrate any changes to the cellular genome that could result in oncogenesis.

Fusion Transcripts and Readthrough

NrLAM-PCR can be used to analyse vector/host fusion transcripts and read-through transcripts as well as integration sites.

(nr)LAM-PCR, 454 sequencing and bioinformatical data analysis are described by Schmidt et al. (2007), Paruzynski et al. (2010) and Arens et al. 2012).

Figure 6:
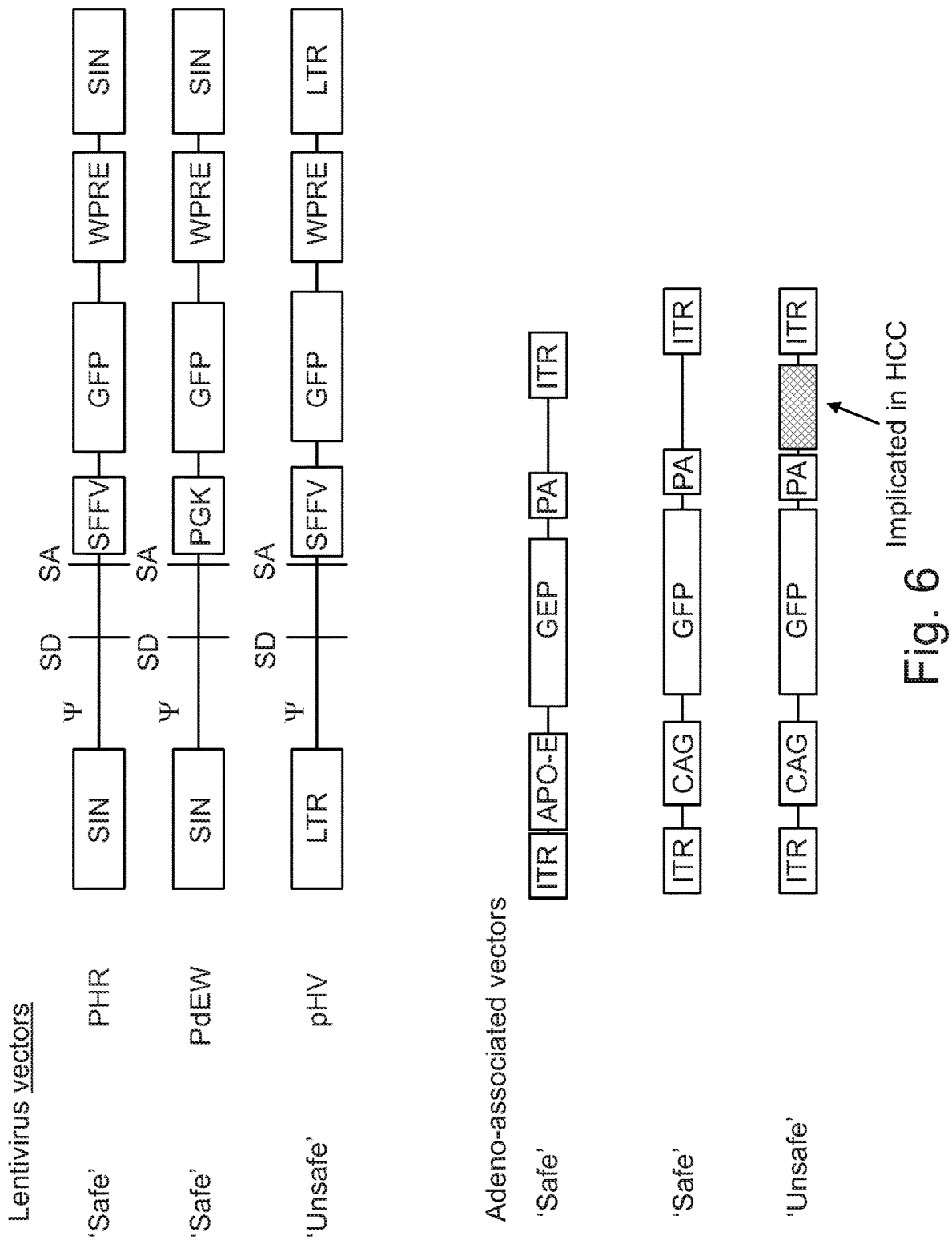
FIG. 6 shows examples of LV and AAV vector 'standards'.

Adjustments to these protocols are described by Scholz et al. (2017). These data describe the identification of vectors IS, vector/host splicing and read-through transcripts as genotoxicity contributory factors that are accepted to cause oncogenesis. For the analysis, vector 'standards' are used that have been shown to cause and not cause this genotoxicity. Examples of these LV and AAV vector 'standards' are shown in FIG. 6. These LV 'standards' LV are described by Scholz et al. (2017) and by Bokhoven et al. (2009).

The examples of LV and AAV standards shown in FIG. 6 are considered as 'safe' or 'unsafe' with regards to genotoxicity potential. The PHR and PdEW vectors are self inactivating (SIN) configuration. This means that the LTR promoter activity is abolished and therefore after integration, IS genes cannot be changed in their expression. The pHV vector has a complete LTR configuration and can cause increased gene expression to IS genes. The 'safe' AAV vectors do not have the promoter region shown in black in the 'unsafe' vector. This region contains a promoter that has been found implicated in hepatocellular carcinoma in mice (Chandler et al. (2016)).

LV and AAV vectors that have configurations that enable them to be used as 'standards' for genotoxicity are valuable to the model described here. These vectors are used to align with vectors under investigation for their IS selection, splicing with the host genome and read-through after integration. These factors are used as a measure of genotoxicity potential. It is preferred that a safe vector does not activate or inactivate gene expression, does not splice with the host and shows no read-through. Measurements of these parameters will be suggestive of genotoxicity potential but not an absolute accurate guarantee that can predict genotoxicity in a human for their lifetime.

The skilled person will appreciate that modifications can be made to the above description of the preferred embodiment.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in United Kingdom patent application 1711065.1, from which this application claims priority, and in the accompanying abstract are incorporated herein by reference.

REFERENCES

Arens et al. (2012) Bioinformatical clonality analysis of next generation sequencing derived viral vector integration sites. *Hum. Gene Ther. Methods* 23, 111-8.

Bokhoven et al. (2009) Insertional gene activation by lentiviral and gammaretroviral vectors. *J. Virol.* 83, 283-294.

Chandler et al. Genotoxicity in mice following AAV gene delivery: A safety concern for human gene therapy? *Mol. Ther.* 24, 198-201.

Godoy et al. (2016) Corrigendum to "Gene networks and transcription factor motifs defining the differentiation of human stem cells into hepatocyte-like cells" [*J. Hepatol.* 2015; 63:934-42] *J. Hepatol.* 64, 525-6.

Kane et al. (2010) Lentivirus-mediated reprogramming of somatic cells in the absence of transgenic transcription factors. *Mol. Ther.* 18, 2139-45.

Kustikova et al. (2009) Cell-intrinsic and vector-related properties cooperate to determine the incidence and consequences of insertional mutagenesis. *Mol. Ther.* 17, 1537-47.

Montini et al. (2006) Hematopoietic stem cell gene transfer in a tumor-prone mouse model uncovers low genotoxicity of lentiviral vector integration. *Nat. Biotechnol.* 24: 687-96.

Nowrouzi et al. (2013) The fetal mouse is a sensitive genotoxicity model that exposes lentiviral-associated mutagenesis resulting in liver oncogenesis. *Mol. Ther.* 21, 324-37.

Paruzynski et al. (2010) Genome-wide high-throughput integrome analyses by nrLAM-PCR and next-generation sequencing. *Nat. Protoc.* 5, 1379-95.

Schmidt et al. (2002) Polyclonal long-term repopulating stem cell clones in a primate model. *Blood* 100:2737-43.

Schmidt et al. (2003) Clonality analysis after retroviral-mediated gene transfer to CD34+ cells from the cord blood of ADA-deficient SCID neonates. *Nat. Med.* 9, 463-8.

Schmidt et al. (2007) High-resolution insertion-site analysis by linear amplification-mediated PCR (LAM-PCR). *Nat. Methods* 4, 1051-57.

Scholz et al. (2017) Lentiviral vector promoter is decisive for aberrant transcript formation. *Hum. Gene Ther.* 28, 875-885.

Themis et al. (2005) Oncogenesis following delivery of a nonprimate lentiviral gene therapy vector to fetal and neonatal mice. *Mol. Ther.* 12, 763-71.

Wu et al. (2003) Transcription start regions in the human genome are favored targets for MLV integration. *Science* 300, 1749-51.

The invention claimed is:

1. A method of determining the safety of an integrating gene therapy vector including:
   infecting a culture of induced pluripotent stem cells with an integrating gene therapy vector;
   allowing the induced pluripotent stem cells to differentiate;
   infecting the cells with the integrating gene therapy vector at least once during differentiation;
   extracting nucleic acids from some of the infected cells after each infection; and
   performing multiple assays on the extracted nucleic acids for each infection, wherein the assays include two or more of:
   (i) an integration site assay to determine vector insertion sites in the host genome,
   (ii) a gene expression assay to determine changes in gene expression over time,
   (iii) an RNA transcript assay to identify new transcripts or truncated transcripts over time,
   (iv) a CpG methylation assay of genes at the integration site, and
   (v) a gene inactivation assay, and
   comparing the results obtained from the assays to a culture of induced pluripotent stem cells that have not been infected by the vector at the different time points.

2. The method as claimed in claim 1, wherein the culture is infected by the gene therapy vector at two or more different time points during differentiation.

3. The method as claimed in claim 1, wherein different amounts of vector are used in each infection.

4. The method as claimed in claim 1, wherein each infecting step includes exposing the cells to vector for at least 30 minutes.

5. The method as claimed in claim 1, wherein each infecting step includes exposing the cells to vector for at least 3 hours.

6. The method as claimed in claim 1, wherein each infecting step includes exposing the cells to vector overnight.

7. The method as claimed in claim 1, wherein the vector is a virus or plasmid.

8. The method as claimed in claim 7, wherein the vector is a retrovirus.

9. The method as claimed in claim 8, wherein the vector is a lentivirus.

10. The method as claimed in claim 7, wherein the vector is an adeno-associated virus.

11. The method as claimed in claim 1, wherein the induced pluripotent stem cells are derived from a human or mouse.

12. The method as claimed in claim 11, wherein the induced pluripotent stem cells are derived from cells of an individual in need of gene therapy.

13. The method as claimed in claim 1, wherein the vector carries a corrected gene required by an individual.

14. The method as claimed in claim 13, wherein the vector further carries nucleic acid elements needed for expression of the corrected gene.

15. The method as claimed in claim 1, wherein the cells are infected by the gene therapy vector in their terminally differentiated form.

16. The method as claimed in claim 1, wherein the integration site assay comprises ligation adaptor mediated PCR, target enrichment sequencing and/or inverse PCR.

17. The method as claimed in claim 1, wherein the gene expression assay is done by RNASeq.

18. The method as claimed in claim 1, wherein the gene expression assay is done by quantitative RT-PCR (reverse transcription polymerase chain reaction).

19. The method as claimed in claim 1, wherein the CpG methylation assay is carrying out using an ELISA (enzyme-linked immunosorbent assay).

* * * * *